United States Patent [19]
Kaul et al.

[11] Patent Number: 4,964,152
[45] Date of Patent: Oct. 16, 1990

[54] PORTABLE X-RAY DIAGNOSTICS APPARATUS HAVING A HEIGHT-ADJUSTABLE COLUMN

[75] Inventors: Karlheinz Kaul, Uttenreuth; Edmund Saffer, Eggolsheim; Hans-Christian Bock, Uttenreuth, all of Fed. Rep. of Germany

[73] Assignee: Siemens Aktiengesellschaft, Berlin and Munich, Fed. Rep. of Germany

[21] Appl. No.: 411,738

[22] Filed: Sep. 25, 1989

[30] Foreign Application Priority Data

Oct. 13, 1988 [EP] European Pat. Off. ........ 88117043.5

[51] Int. Cl.⁵ .............................................. H05G 1/02
[52] U.S. Cl. .................................... 378/198; 378/197
[58] Field of Search ................ 378/198, 197, 195, 196

[56] References Cited

U.S. PATENT DOCUMENTS 2,168,209  8/1939  Haupt ................................. 378/197
4,387,468  7/1983  Fenne et al. ........................ 378/198

FOREIGN PATENT DOCUMENTS 1958905  6/1971  Fed. Rep. of Germany .
2640644  3/1978  Fed. Rep. of Germany .
525656   6/1921  France ................................. 378/198

Primary Examiner—Craig E. Church
Attorney, Agent, or Firm—Hill, Van Santen, Steadman & Simpson

[57] ABSTRACT

A portable x-ray diagnostics apparatus has a radiation receiver mounted at one end of a height-adjustable column by a support mount. The lower, opposite end of the column is attached to a wheeled base of the apparatus. A height-adjustment mechanism is provided inside the column and the base which permits the height of the x-radiator above the base to be adjusted without an electromotive drive, and such that the force exerted for adjusting the height of the column is substantially the same over the entire adjustment path. For this purpose, one end of a cable is connected at a location inside the lower end of the column, and the cable is guided around various deflection elements, with the opposite end being attached in the base of the apparatus. A weight compensating force is provided by a spring connected to one of the deflection elements, with the spring being horizontally tensed in the base of the apparatus.

6 Claims, 1 Drawing Sheet

PORTABLE X-RAY DIAGNOSTICS APPARATUS HAVING A HEIGHT-ADJUSTABLE COLUMN

BACKGROUND OF THE INVENTION

1. Field of the Invention

The present invention relates to portable x-ray diagnostics devices of the type having a height-adjustable column.

2. Description of the Prior Art

A portable x-ray diagnostics apparatus is described in German Patent No. 1 958 805 having a column which is height adjustable by an electromotive drive, with a lower portion of the column mounted on a carriage, and an x-radiator and a radiation receiver carried on a support mount which is attached to an upper end of the column.

For adjusting the height of the column in this known apparatus, electrical energy is required from the mains or from an storage battery, as a power supply for the electromotive drive. If voltage is obtained from the mains, a supply line and a transformer must be provided. If energy is obtained from a storage battery, the carriage of the x-ray diagnostics apparatus must be designed to accommodate the weight and dimensions of the storage battery.

SUMMARY OF THE INVENTION

It is an object of the present invention to provide a portable x-ray diagnostics apparatus having a height adjustable column in which adjustment of the height of the column can be accomplished without an electromotive drive, and having a simple, space-saving structure.

The above object is achieved in a portable x-ray diagnostics apparatus having a cable with one end connected to a lower end of the column, and being conducted around a number of deflection elements inside a carriage of the apparatus which receives the column, with an opposite end of the cable being attached at a lower portion inside the base of the carriage. A weight-compensating force is exerted on the column via the cable, which is generated by a spring which is horizontally tensed in the base of the carriage of the apparatus.

An advantage of this structure is that the column can be adjusted in height in a weight-compensated fashion without the expenditure of electrical energy. This is particularly advantageous when moving the x-ray diagnostics apparatus to a station, if the column, with the x-radiator and the radiation receiver mounted thereon, has not been previously moved to the lowest position after conducting the last x-ray exposure. In prior art devices, a cord for supplying energy to the electromotive drive must be plugged into an electrical supply in order to move the column to its lowest position before moving the apparatus. Under certain circumstances, such a connection is not within easy reach, so that the x-ray diagnostics apparatus must first be moved to a location at which the electrical connection can be made, before the actual move to the next station can be continued. If a battery is used in the prior art devices, the added weight and dimensions of the battery make the unit heavier and more bulky, thereby impeding easy transfer of the apparatus from station to station. By contrast, the column in the portable x-ray diagnostics apparatus disclosed herein can be adjusted as needed without supplying electrical energy thereto.

In a further embodiment of the invention, a brake is provided for arresting the column. The column can be arrested at any arbitrary position along its displacement path. In another embodiment, the brake can be constructed so that movement of the column is automatically arrested when the x-ray diagnostics apparatus tilts.

DESCRIPTION OF THE PREFERRED EMBODIMENTS

Figure 1:
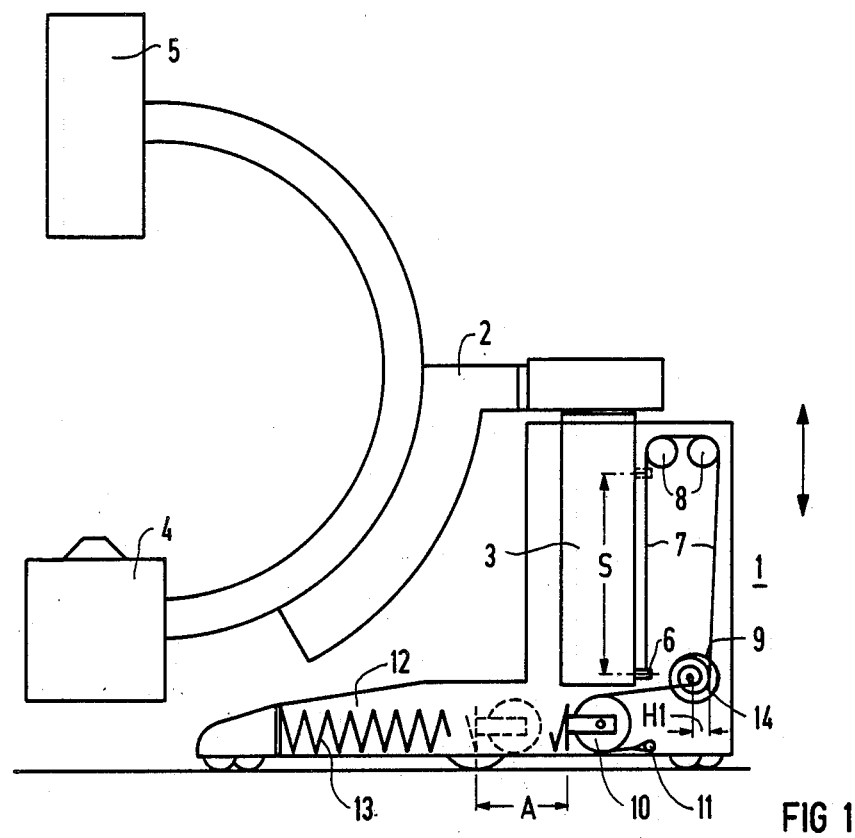
FIG. 1 is a side view, partly in section, of a portable x-ray diagnostics apparatus having a height-adjustable column constructed in accordance with the principles of the present invention.

A portable x-ray diagnostics apparatus is shown in FIG. 1, partly in section to expose components for explaining the subject matter of the invention. The apparatus 1 has a support mount 2, which is height-adjustable relative to a carriage by means of a column 3. An x-radiator 4 and a radiation reciever 5 are attached to the mount 2.

The column 3 is received in a carriage of the apparatus, and has a lower end connected to a cable 7 inside the carriage by an attachment element 6. The column 7 is conducted, inside the carriage, around a first deflection means 8, consisting of two rollers, and around a second deflection means 9. The deflection means 9 is a truncated conical drum, with a helical groove 14 therein in which the cable 7 is received. The cable 7 continues around a third deflection means 10, and is fastened by a fastening element 11 in a lower region of the carriage, such as in the base.

The third deflection means 10 is a roller and is connected to a pre-stressed coil spring 13, horizontally disposed in the base 12 of the carriage. As a consequence of the tensed coil spring 13, a tensile force acts on the cable 7, which compensates for the weight of the column 3, and of the support mount with the x-radiator 4 and the radiation receiver 5 mounted thereon.

The helical groove 14 of the second deflection means 9 is fashioned so that, in combination with the tensile force of the coil spring 13, the force for adjusting the column 3 is uniform over the entire adjustment path S of the column 3. Because the tensile force of the column spring 13 varies dependent upon its extension A, the weight compensating force would be non-uniform, if further measures were not taken. A substantially constant adjustment force is achieved by suitable selection of the radii H1 and H2 of the second deflection means 9. The radus H1 is the distance between the center axis of rotation of the deflection means 9 and the location at which the cable 7 departs from the helical groove 14. The radius H2 is the distance between the center axis 10 of the deflection means 9 and the location at which the cable 7 enters the helical groove 14. These radii constitute lever arms for calculating the torque acting on the cable 7, which determines the amount of weight-compensation acting on the column 3. As the deflection means 9 rotates, the lever arms represented by the radii H1 and H2 change, decreasing as the extension A increases. This results in the torque exerted on the cable 7 being substantially constant over the adjustment path S of the column 3.

Figure 2:
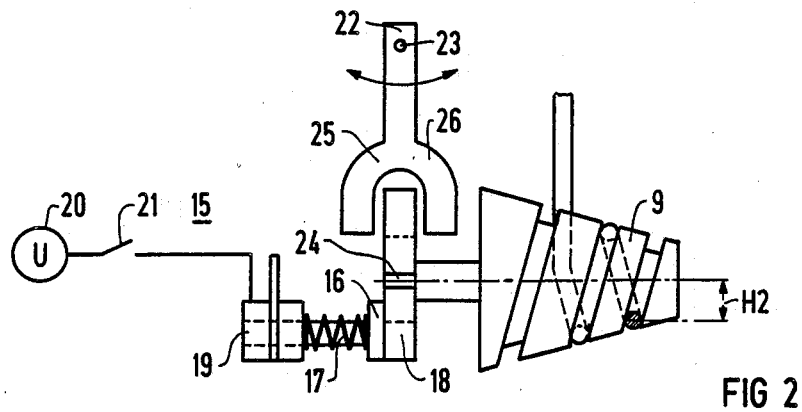
FIG. 2 is a side view showing details of a conical drum and a brake mechanism for the height-adjustable column of the apparatus of FIG. 1.

Locking of the column 3 is achieved with a brake mechanism 15, shown in one embodiment in FIG. 2.

The brake mechanism 15 includes a brake shoe 16, which is pressed against a brake disk 18 by the force of a coil spring 17. The brake disk 18 is mechanically connected to the deflection means 9. Instead of a coil spring 17, however, a permanent magnet may be used to act on the brake shoe 16. When the brake shoe 16 is against the brake disk 18, the column 3 is locked in position. In the embodiment shown in FIG. 2, the brake mechanism 15 is released by a voltage from a voltage source 20 being supplied to an electromechanical drive 19 via a switch 21, causing the brake shoe 16 to move away from the brake disk 18, so that the deflection means 9 is again freely adjustable. It is also possible to move the brake shoe 16 away from the brake disk 18 by a mechanical actuation means (not shown) located on the carriage of the apparatus 1. This permits the brake to be released without the supply of electrical energy thereto.

A fork-shaped element 22 is adjustably mounted transversely relative to the brake disk 18, by means of a bearing 23. The brake disk 18 has recesses 24 in the circumference thereof. One of the legs 25 or 26 of the fork-shaped element 22 will engage in one of the recesses 24 given lateral tilting of the x-ray diagnostics apparatus 1, so that movement of the column 3 under those conditions is blocked. When the carriage is again substantially upright, the fork-shaped element 22 will again assume a substantially vertical position, in which it does not interfere with rotation of the brake disc 18.

Although modifications and changes may be suggested by those skilled in the art, it is the intention of the inventors to embody within the patent warranted hereon all changes and modifications as reasonably and properly come within the scope of their contribution to the art.

We claim as our invention:

1. A mobile x-ray diagnostics apparatus comprising:
    a carriage having a vertical portion and a horizontal base;
    a height-adjustable column slidably received in said vertical portion of said carriage and having an x-radiator and a radiation receiver mounted thereon;
    a cable disposed inside said carriage and having one end attached to a lower region of said column in said carriage;
    a plurality of deflection elements in said carriage around which said cable is entrained, said cable having an opposite end attached inside said carriage; and
    a horizontally tensed spring disposed and anchored in said base of said carriage and attached to one of said deflection elements for exerting a weight-compensating force on said column via said cable.

2. A mobile x-ray diagnostics apparatus as claimed in claim 1, wherein said plurality of deflection elements comprise a first deflection element disposeed in an upper region of said vertical portion of said carriage, a second deflection element disposed in a lower region of said vertical portion of said carriage, and a third deflection element attached to said spring.

3. A mobile x-ray diagnostics apparatus as claimed in claim 1, wherein said spring has a length over which it is extensible and wherein one of said deflection elements is a truncated conical drum having a helical groove therein receiving said cable so that said weight-compensating force on said column is substantially the same over said extensible length of said spring.

4. A mobile x-ray diagnostics apparatus as claimed in claim 1, further comprising:
    brake means disposed in said carriage for arresting movement of said column relative to said carriage.

5. A mobile x-ray diagnostics apparatus as claimed in claim 4, wherein said brake means is attached to one of said deflection elements.

6. A mobile x-ray diagnostics apparatus as claimed in claim 4, wherein said brake means includes means for arresting movement of said column relative to said carriage when said carriage is laterally tilted.

* * * * *